(12) United States Patent
Colin et al.

(10) Patent No.: US 6,263,743 B1
(45) Date of Patent: Jul. 24, 2001

(54) LIQUID TRANSFERRING DEVICE

(75) Inventors: Bruno Colin, Marcy l'Etoile; Cécile Jaravel, Lyons, both of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/202,618

(22) PCT Filed: May 5, 1998

(86) PCT No.: PCT/FR98/00903

§ 371 Date: Dec. 18, 1998

§ 102(e) Date: Dec. 18, 1998

(87) PCT Pub. No.: WO98/50155

PCT Pub. Date: Nov. 12, 1998

(30) Foreign Application Priority Data

May 5, 1997 (FR) .................................................. 97/05785

(51) Int. Cl.⁷ ...................................................... G01N 1/00
(52) U.S. Cl. ............................................................ 73/864.85
(58) Field of Search ........................... 73/864.81, 864.85, 73/864.87, 864.21, 863.11; 141/311 R, 363, 365, 366

(56) References Cited

U.S. PATENT DOCUMENTS 2,955,627 * 10/1960 Gaskins .
4,585,623    4/1986 Chandler .
5,010,928 *  4/1991 Ballas .

FOREIGN PATENT DOCUMENTS

| 0 381 501 A2 | 8/1990 | (EP) . |
| 0 701 865 A1 | 3/1996 | (EP) . |
| A-7-80331 | 3/1995 | (JP) . |
| WO 83/01912 | 6/1983 | (WO) . |
| WO 93/02795 | 2/1993 | (WO) . |
| WO 93/09431 | 5/1993 | (WO) . |

* cited by examiner

Primary Examiner—Robert Raevis
(74) Attorney, Agent, or Firm—Oliff & Berridge PLC

(57) ABSTRACT

A device for transferring a liquid sample drawn by suction, through a wall having an orifice, the device including a conduit, a plunger sealingly sliding in the conduit, and a rod controlling the plunger. The device includes a joining piece extending the conduit, with an outer cross-section adapted to fit in the aperture, for example sealing it, with close working clearance required for inserting the joining piece in the orifice, the joining piece being arranged to be separated from the conduit once it is engaged in the orifice, and to seal the orifice, when or once the joining piece engaged in the orifice is separated from the conduit.

30 Claims, 1 Drawing Sheet

US 6,263,743 B1

LIQUID TRANSFERRING DEVICE

BACKGROUND OF THE INVENTION

1. Field of the Invention

The present invention relates generally to a device for transferring a liquid sample, drawn by suction, through a wall comprising an orifice which passes through the wall.

2. Description of the Related Art

Various devices which make it possible, in a first stage, to suck up a liquid sample and, in a second stage, to expel all or part of this sample are already known and generally comprise, principally, a conduit, a plunger sealingly sliding in said conduit and a rod controlling said plunger, particularly manually, or an equivalent means.

SUMMARY OF THE INVENTION

The subject of the present invention is a transferring device which has the above-defined arrangement but which by itself makes it possible, after transfer, to seal or close off the orifice through which the liquid drawn by suction has subsequently been expelled.

Starting from a wall as defined above, i.e. comprising the calibrated orifice passing right through it, and through which the sample drawn is expelled, the device according to the invention comprises a joining piece extending the conduit, in the bore of which the plunger slides, with outer cross section adapted to fit in the orifice, for example sealing it, with the close working clearance required for inserting the joining piece in this orifice. This joining piece is arranged on the one hand to be separated from the conduit, by any appropriate means, for example mechanical and/or thermal, once it is engaged in the aforesaid orifice and, on the other hand, to seal the orifice when or once the joining piece engaged in the orifice is separated from the conduit.

Preferably, to seal the orifice, the relatively hard plunger is arranged to constrain or crush the relatively soft wall of the joining piece between itself and the relatively stiff wall of said orifice, whereby said joining piece forms a definitive annular seal, when or once said joining piece and with plunger engaged in said orifice are separated from said conduit and the control rod, respectively.

In a particularly advantageous manner, especially in the field of biology, the joining piece is produced from a material, for example a plastics material, capable of melting through the effect of heat. By virtue of this supplementary means, and when a thermal means is used to separate the conduit from the joining piece, and optionally the control rod of the plunger, not only does the melting of the joining piece contribute to or allow sealing of the orifice but, also, this same thermal means sterilizes or decontaminates the sealed orifice on the one hand and the rest of the transferring device on the other, i.e. its end remote from the joining piece and, possibly, the plunger, whereby this remainder or waste may be disposed of in sterile or decontaminated condition.

By virtue of the invention, the joining piece at least serves not only for expelling the liquid drawn by suction but also for sealing the orifice in the wall, for example definitively, and doing so in a leaktight manner.

Applied, for example, to a biological analysis card including a wall such as that defined above, separating a cavity for receiving the drawn liquid sample for analysis from the outside, the invention makes it possible, after insertion of the sample in the analysis card, definitively and completely to isolate the analysis card from the outside, thereby, in particular, preventing any subsequent contamination towards the inside of the analysis card or towards the outside of the latter. This isolation is obtained particularly simply, with no other means or tool, for example, solely with the device itself.

BRIEF DESCRIPTION OF THE DRAWINGS

The present invention is now described with reference to the appended drawings, in which.

DETAILED DESCRIPTION OF PREFERRED EMBODIMENTS

Figure 1:
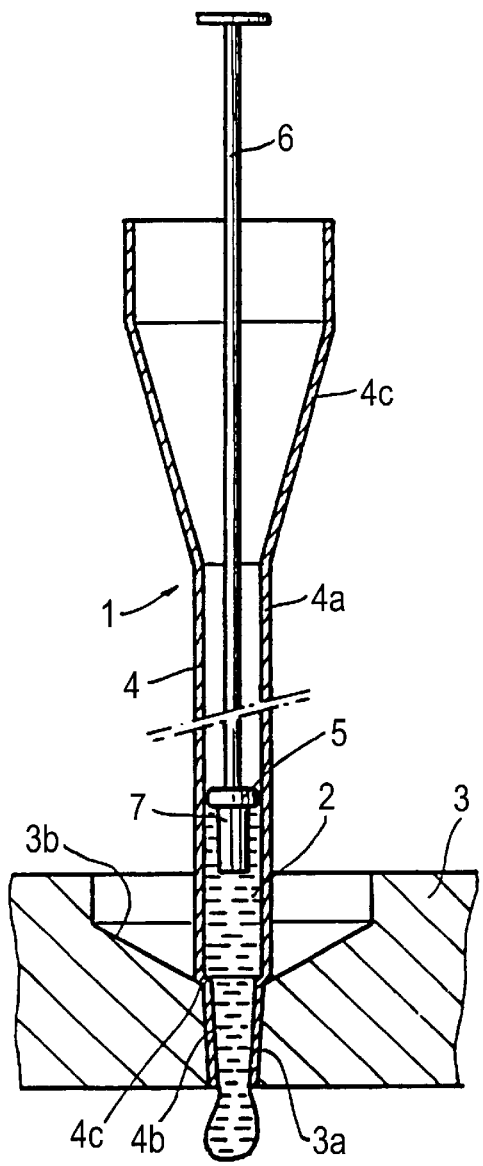
FIG. 1 shows a sectional view of a transferring device according to the invention, coupled in some manner in the orifice in a wall, during expulsion of the liquid previously drawn by suction.

In accordance with FIG. 1, a wall 3, shown diagrammatically or symbolically, includes a frustoconical orifice 3a, with a recess 3b for the penetration and guiding of the joining piece of the transferring device. This is, for example, the wall of an analysis card separating, on the one hand (top of FIG. 1), the outside of the card from the inside of the card (bottom of FIG. 1).

The transferring device 1 comprises a tube 4, made in a monobloc manner, for example by moulding or extrusion of a plastics material, which includes a distal section 4c in the shape of a funnel, a first section 4a forming a cylindrical conduit and a second section 4b forming a joining piece, the sections 4a and 4b being separated by a shoulder 4c bearing against the wall 3.

The joining piece 4b consequently extends the conduit 4a and has an outer cross section, for example a frustoconical outer cross section, adapted to fit in the orifice 3a, which is also of frustoconical shape, for example to seal it, naturally with the close working clearance required for inserting the joining piece 4b in this orifice 3a. This joining piece 4b has a length such that its free end is flush with the lower face of the wall 3.

Given its constituent material, namely a relatively soft, meltable thermoplastic material, for example polyethylene, this joining piece 4b is arranged firstly to be separated from the conduit 4a, by any appropriate means, for example a metal wire for cutting at high temperature; secondly, as described below, the joining piece 4b may be constrained, gripped or crushed in the manner of an annular leaktight seal; thirdly, this joining piece is capable of melting through the effect of heat in order to supplement or to obtain sealing of the orifice 3a, when or once the joining piece 4b engaged in the orifice 3a is separated from the conduit 4a. Of course, separation and melting may be obtained concomitantly, for example by the passage of a high-temperature wire cutting the tube 4 into two parts 4a and 4b and melting the wall of the joining piece 4b in contact with the wall of the orifice 3a and optionally in contact with an inner sealing element described below, in this case the plunger 5.

A plunger 5 is associated with the conduit 4a and sealingly slides in the latter. A control rod 6 on the one hand and a front lengthening piece 7 with a length and cross section adapted for insertion in the joining piece 4b, on the other, are arranged on either side of the plunger 5, in a monobloc manner with the latter, whereas the joining piece 4b is engaged in the orifice 3a (cf. FIG. 2). This monobloc component, associating the control rod 6, the plunger 5 and the front lengthening piece 7, is produced from a technical thermoplastic material which is relatively hard and different from that of the tube 4, for example from polyamide.

Figure 2:
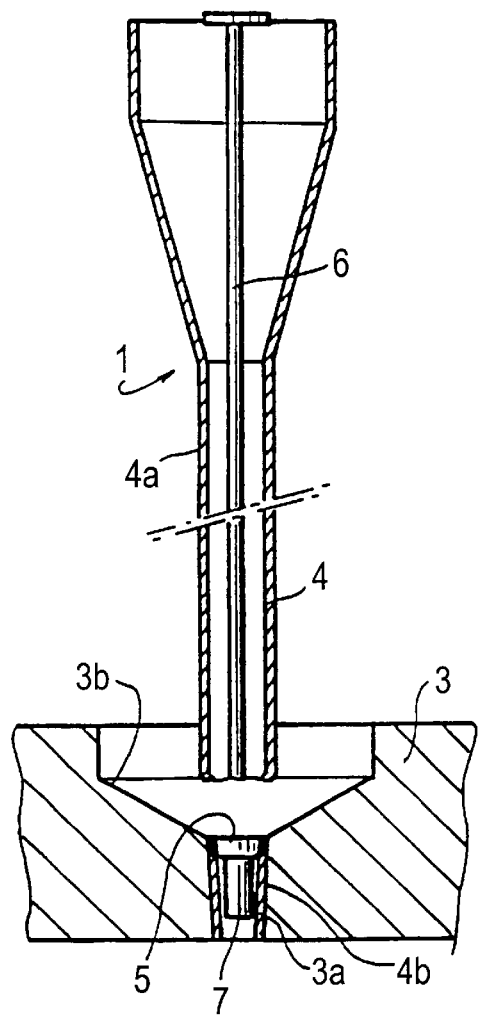
FIG. 2 shows this same transferring device, after complete expulsion of the drawn liquid, separation of the device into two parts, one of which remains in the aforesaid wall, and melting of the joining piece which remained in the wall, while sealing or closing the orifice in the latter, via which the drawn liquid has been transferred.

The plunger 5 consequently separates the control rod 6 from the front lengthening piece 7 and is arranged to constrain or crush the wall of the joining piece 4b between itself and the relatively stiff wall of the orifice 3a, obviously in the position in which the plunger is fitted into the upper part of the joining piece 4b and the lengthening piece 7 engages in the joining piece 4b (cf., also FIG. 2).

By virtue of the meltable, thermoplastic nature of the aforesaid monobloc component, the front lengthening piece 7 and the plunger 5 may be separated from the control rod 6 when they engage in the joining piece 4b, at the same time as the latter is separated from the conduit 4a, this taking place via the same means as those described above, for example a hot metal wire, for cutting.

Under these conditions, the whole of the joining piece 4b, the plunger 5 and the front lengthening piece 7 may be totally separated from the rest of the device using simple mechanical and/or thermal means. This separation takes place after or during definitive sealing of the orifice 3a by virtue, especially, of the melting of the plastics material of the joining piece 4b and, possibly, of the front lengthening piece 7 engaged in the inner cross section of the joining piece 4b.

The method in which the above-described device is used is deduced from the above description:

in the position in which it is not coupled to the wall 3, and extracting the control rod 6 from the conduit 4a, a liquid sample 2 is drawn by suction by means of the joining piece 4b;

this sample then being contained in the tube 4, the transferring device 1 is coupled or assembled in a leaktight manner in the wall 3 and, more precisely, the joining piece 4b is coupled or assembled in the orifice 3a;

now, by pushing the control rod 6 in, the liquid sample 2 is expelled, still via the joining piece 4b;

once the liquid sample has been expelled, still pushing in the control rod 6, the plunger 5 fits into the upper part of the joining piece 4b which results in sealing of the orifice 3a by means of compression of the joining piece 4b between the plunger 5 and the wall of said orifice;

once the plunger 5 is fitted in, the transferring device is separated into two parts with a means such as described above, namely a first part including the joining piece 4b, the plunger 5 and the front lengthening piece 7, remaining in the orifice 3a, and a second part which is released, it being possible for this to be disposed of as waste;

this separation, preferably carried out using a heat source, causes the joining piece 4b and/or the plunger 5 and/or the front lengthening piece 7 to melt, which creates a plug in the orifice 3a which, once solidified, is definitive.

What is claimed is:

1. A device for transferring a liquid sample through a wall comprising an orifice, said device comprising:
    a conduit;
    a plunger sealingly sliding in said conduit; and
    a joining piece, extending the conduit, with an outer cross section adapted to be inserted into said orifice, said joining piece being produced from a meltable material, wherein said joining piece is separated from said conduit and sealed to said orifice by melting the joining piece, when or once said joining piece engages said orifice.

2. The device of claim 1, wherein said meltable material is a plastics material.

3. The device of claim 1, wherein the conduit and the joining piece are produced in a monobloc manner in the form of one single tube, comprising a first section forming a conduit and a second section forming a joining piece.

4. The device of claim 3, wherein the plunger is arranged to constrain or crush the wall of the joining piece between itself and the wall of the orifice when or once said joining piece and said plunger engaged in said orifice are separated from said conduit and from the control rod, respectively.

5. The device of claim 3, wherein the first section and the second section are separated by a shoulder bearing against the wall.

6. The device of claim 5, wherein the plunger is arranged to constrain or crush the wall of the joining piece between itself and the wall of the orifice when or once said joining piece and said plunger engaged in said orifice are separated from said conduit and from the control rod, respectively.

7. The device of claim 1, wherein the control rod is extended by a front lengthening piece with a length and cross section adapted for insertion in said joining piece, when the latter is engaged in said orifice.

8. The device of claim 7, wherein the plunger is arranged to constrain or crush the wall of the joining piece between itself and the wall of the orifice when or once said joining piece and said plunger engaged in said orifice are separated from said conduit and from the control rod, respectively.

9. The device of claim 7, wherein said front lengthening piece is arranged to be separated from the control rod when they engage in said joining piece, at the same time as the latter is separated from the conduit.

10. The device of claim 9, wherein said front lengthening piece is arranged to be separated from the control rod with the plunger.

11. The device of claim 9, wherein the control rod and the front lengthening piece and optionally the plunger, are monobloc and produced from a meltable material.

12. The device of claim 11, wherein said meltable material is a plastics material.

13. The device of claim 7, wherein the plunger separates the control rod from the front lengthening piece.

14. The device of claim 7, wherein the plunger separates the control rod from the front lengthening piece.

15. The device of claim 1, wherein the plunger is arranged to constrain or crush the wall of the joining piece between itself and the wall of the orifice when or once said joining piece and said plunger engaged in said orifice are separated from said conduit and from the control rod, respectively.

16. The device of claim 1, wherein the joining piece has a length such that its free end is flush with one of the faces of the wall.

17. The device of claim 1, wherein said outer cross section of said joining piece is adapted to seal said orifice.

18. A device for transferring a liquid sample through a wall comprising an orifice, said device comprising:
   a conduit;
   a plunger sealingly sliding in said conduit;
   a rod controlling said plunger; and
   a joining piece extending the conduit with an outer cross section adapted to be inserted into said orifice, wherein the plunger is arranged to constrain or crush the wall of the joining piece between itself and the wall of the joining piece, and thus to seal said orifice when said plunger engages said joining piece, and wherein said joining piece is arranged so as to be separated from said conduit by thermal or mechanical means.

19. The device of claim 15, wherein the conduit and the joining piece are produced in a monobloc manner in the form of one single tube, comprising a first section forming a conduit and a second section forming a joining piece.

20. The device of claim 19, wherein the first section and the second section are separated by a shoulder bearing against the wall.

21. The device of claim 20, wherein the plunger constrains or crushes the wall of the joining piece between itself and the wall of the orifice when or once said joining piece and said plunger engaged in said orifice are separated from said conduit and from the control rod, respectively.

22. The device of claim 15, wherein the control rod is extended by a front lengthening piece with a length and cross section adapted for insertion in said joining piece, when the latter is engaged in said orifice.

23. The device of claim 22, wherein said front lengthening piece is arranged to be separated from the control rod when they engage in said joining piece, at the same time as the latter is separated from the conduit.

24. The device of claim 23, wherein said front lengthening piece is arranged to be separated from the control rod with the plunger.

25. The device of claim 22, wherein the plunger separates the control rod from the front lengthening piece.

26. The device of claim 22, wherein the plunger constrains or crushes the wall of the joining piece between itself and the wall of the orifice when or once said joining piece and said plunger engaged in said orifice are separated from said conduit and from the control rod, respectively.

27. The device of claim 22, wherein the plunger separates the control rod from the front lengthening piece.

28. The device of claim 15, wherein the plunger constrains or crushes the wall of the joining piece between itself and the wall of the orifice when or once said joining piece and said plunger engaged in said orifice are separated from said conduit and from the control rod, respectively.

29. The device of claim 15, wherein the joining piece has a length such that its free end is flush with one of the faces of the wall.

30. The device of claim 15, wherein said outer cross section of said joining piece is adapted to seal said orifice.

* * * * *